United States Patent
Krause et al.

(10) Patent No.: US 9,556,433 B2
(45) Date of Patent: Jan. 31, 2017

(54) NUCLEIC ACIDS FOR DOWN-REGULATION OF GENE EXPRESSION

(71) Applicants: UNIVERSITE DE GENEVE, Geneva (CH); UNIVERSITY OF PRETORIA, Pretoria (ZA)

(72) Inventors: Karl-Heinz Krause, Geneva (CH); Renier Myburgh, Pretoria (ZA); Patrick Salmon, Geneva (CH)

(73) Assignees: Université de Genève, Genève (CH); University of Pretoria, Pretoria (ZA)

( * ) Notice: Subject to any disclaimer, the term of this patent is extended or adjusted under 35 U.S.C. 154(b) by 0 days.

(21) Appl. No.: 14/415,201

(22) PCT Filed: Sep. 13, 2013

(86) PCT No.: PCT/IB2013/058545
§ 371 (c)(1),
(2) Date: Jan. 16, 2015

(87) PCT Pub. No.: WO2014/016817
PCT Pub. Date: Jan. 30, 2014

(65) Prior Publication Data
US 2015/0176006 A1 Jun. 25, 2015

(51) Int. Cl.
*C12N 15/113* (2010.01)
*C12N 15/11* (2006.01)

(52) U.S. Cl.
CPC ............ *C12N 15/113* (2013.01); *C12N 15/111* (2013.01); *C12N 2310/11* (2013.01); *C12N 2310/141* (2013.01); *C12N 2310/344* (2013.01); *C12N 2310/531* (2013.01); *C12N 2310/533* (2013.01); *C12N 2330/30* (2013.01)

(58) Field of Classification Search
None
See application file for complete search history.

(56) References Cited

U.S. PATENT DOCUMENTS

2010/0068814 A1   3/2010 Zhu et al.

FOREIGN PATENT DOCUMENTS

| WO | WO 2007/053184 | 5/2007 | |
| WO | WO 2008/150897 | 12/2008 | |
| WO | WO 2008150897 A2 * | 12/2008 | ............ C12N 15/111 |

OTHER PUBLICATIONS

Krol, et al. (2004) "Structural Features of MicroRNA (miRNA) Precursors and Their Relevance to miRNA Biogenesis and Small Interfering RNA/Short Hairpin RNA Design Structural Features of MicroRNA (miRNA) Precursors and Their Relevance to miRNA Biogenesis and Small Interfering RNA/Short Hairpin RNA Design", The Journal of Biological Chemistry, 279(4.*
Myburgh, et al. (2014) "Optimization of Critical Hairpin Features Allows miRNA-based Gene Knockdown Upon Single-copy Transduction", Molecular Therapy—Nucleic Acids, 3: e207 (13 pages long).*
"Get control of you r knockdown experiments. BLOCK-iT™ Pol II miR RNAi expression vectors," Invitrogen, copyright 2 008.
"Thermo Scientific Dharmacon SMARTvector 2.0 Lentiviral shRNA Particles," Thermo Fisher Scientific Inc., copyright 2010.
Mybrugh et al., "Engineering an HIV resistant immune system," 12th Day of Clinical Research, University of Zurich, Apr. 4, 2013. Retrieved from the internet: http://www.usz.ch/nom_cms/zkf/DOCR/abstracts%20Program%2012th%20Day%20of%20Clinical%20Research%2004APR2013.pdf, retrieved on Jan. 28, 2014.
Myburgh et al., "Engineering an HIV resistant immune system in humanized mice," Abstract #31, 4th Swiss Virology Meeting, University of Lausanne, Feb. 5, 2013. Retrieved from the internet at https://www3.unil.ch/swissvirology/Fichiers/AbstractBookSVM2013.pdf, retrieved on Jan. 28, 2014.
PCT International Search Report and Written Opinion issued in International Patent Application No. PCT/IB2013/058545, dated Feb. 10, 2014.
Shan et al., "Comparison of approaches for efficient gene silencing induced by microRNA-based short hairpin RNA and indicator gene expression," *Molecular Biology Reports*, 37(4):1831-1839, 2009.
Yue et al., "A miR-21 hairpin structure-based gene knockdown vector," *Biochemical and Biophysical Research Communications*, 394(3):667-672, 2010.

* cited by examiner

*Primary Examiner* — Robert M Kelly
(74) *Attorney, Agent, or Firm* — Parker Highlander PLLC

(57) ABSTRACT

Recombinant nucleic acid molecules are provided that form hair pin structures and can be used to down-regulate gene expression. For example, a nucleic acid molecule can comprise a flanking and lower stem loop sequence from a mir-16 gene; an antisense target sequence; a mir-30 loop sequence; a complement of the anti-sense target sequence; and a lower stem loop complementary to the mir-16 sequence. Methods for down regulating gene expression in a cell using such recombinant nucleic acid molecules are also provided.

21 Claims, 5 Drawing Sheets

SEQUENCE LISTING

```
<160> NUMBER OF SEQ ID NOS: 9

<210> SEQ ID NO 1
<211> LENGTH: 12
<212> TYPE: DNA
<213> ORGANISM: Artificial Sequence
<220> FEATURE:
<223> OTHER INFORMATION: Synthetic primer

<400> SEQUENCE: 1
ggtgatagca at                                                              12

<210> SEQ ID NO 2
<211> LENGTH: 11
<212> TYPE: DNA
<213> ORGANISM: Artificial Sequence
<220> FEATURE:
<223> OTHER INFORMATION: Synthetic primer

<400> SEQUENCE: 2
cagcagtgcc t                                                               11

<210> SEQ ID NO 3
<211> LENGTH: 12
<212> TYPE: DNA
<213> ORGANISM: Artificial Sequence
<220> FEATURE:
<223> OTHER INFORMATION: Synthetic primer

<400> SEQUENCE: 3
tcagcagtgc ct                                                              12

<210> SEQ ID NO 4
<211> LENGTH: 13
<212> TYPE: DNA
<213> ORGANISM: Artificial Sequence
<220> FEATURE:
<223> OTHER INFORMATION: Synthetic primer

<400> SEQUENCE: 4
gtcagcagtg cct                                                             13
```

```
<210> SEQ ID NO 5
<211> LENGTH: 14
<212> TYPE: DNA
<213> ORGANISM: Artificial Sequence
<220> FEATURE:
<223> OTHER INFORMATION: Synthetic primer

<400> SEQUENCE: 5
cgtcagcagt gcct                                                        14

<210> SEQ ID NO 6
<211> LENGTH: 15
<212> TYPE: DNA
<213> ORGANISM: Artificial Sequence
<220> FEATURE:
<223> OTHER INFORMATION: Synthetic primer

<400> SEQUENCE: 6
acgtcagcag tgcct                                                       15

<210> SEQ ID NO 7
<211> LENGTH: 15
<212> TYPE: DNA
<213> ORGANISM: Artificial Sequence
<220> FEATURE:
<223> OTHER INFORMATION: Synthetic primer

<400> SEQUENCE: 7
gtgaagccac agatg                                                       15

<210> SEQ ID NO 8
<211> LENGTH: 23
<212> TYPE: DNA
<213> ORGANISM: Artificial Sequence
<220> FEATURE:
<223> OTHER INFORMATION: Synthetic primer

<400> SEQUENCE: 8
aagtaaggtt gaccatactc tac                                              23

<210> SEQ ID NO 9
<211> LENGTH: 71
<212> TYPE: DNA
<213> ORGANISM: Homo sapiens

<400> SEQUENCE: 9
gcgactgtaa acatcctcga ctggaagctg tgaagccaca gatgggcttt cagtcggatg      60
tttgcagctg c                                                           71
```

NUCLEIC ACIDS FOR DOWN-REGULATION OF GENE EXPRESSION

This application is a national phase application under 35 U.S.C. §371 of International Application No. PCT/IB2013/058545, filed Sep. 13, 2013, which claims the benefit of United States Provisional Patent Application No. 61/672,441, filed Jul. 17, 2012. The entire contents of the above-referenced disclosures are specifically incorporated herein by reference.

INCORPORATION OF SEQUENCE LISTING

The sequence listing that is contained in the file named "UGENP0017US_ST25.txt, which is 3 KB (as measured in Microsoft Windows®) and was created on Jan, 15, 2015, is filed herewith by electronic submission and is incorporated by reference herein.

BACKGROUND OF THE INVENTION

1. Field of the Invention

The present invention relates generally to the field of molecular biology and biochemistry. More particularly, it concerns methods and compositions for expression of inhibitory RNA molecules.

2. Description of Related Art

RNA interference (RNAi) is a naturally occurring, evolutionary conserved biological process in plants and animals as well as humans. Suppression of gene expression via RNAi occurs either by sequence specific degradation of mRNA molecules, or by interfering with translation of mRNA molecules. These two mechanisms are mediated by small interfering RNA (siRNA) molecules that recognize their complimentary sequences in the mRNA. To describe the natural RNAi pathway in brief, an RNAi gene when transcribed produces a primary micro RNA molecule (pri-miRNA). In the nucleus, the enzyme Drosha recognizes structural elements of the pri-miRNA and cleaves it accordingly to produce a premature mi-RNA (pre-miRNA). Exportin 5 transports the pre-miRNA into the cytoplasm where the enzyme Dicer further cleaves the molecule resulting in a miRNA duplex. One half i.e. one strand of the miRNA duplex is then selected and incorporated into the RNA-induced silencing complex (RISC). In most cases, if the strand of the miRNA duplex selected is 100% complimentary to the target mRNA, cleavage of the mRNA occurs. If the strand of the miRNA duplex selected is not 100% complimentary to the target mRNA, mRNA may not be degraded but RISC will interfere with ribosome function, hence decreasing translation of the protein. In both cases, the resulting decrease of final protein synthesis is termed post-transcriptional gene silencing (PTGS) (He and Hannon, 2004).

Down-regulation of gene expression by use of RNAi is now also being explored as a promising therapeutic tool to address infectious diseases, cancers, as well as inheritable genetic diseases. However, despite significant advances in the field, the magnitude of reduction in gene expression that is achieved with such strategies is often insufficient to provide clinical efficacy. Methods for significant and sustainable targeted reduction of gene expression are therefore still in great need.

SUMMARY OF THE INVENTION

In a first embodiment there is provided a recombinant nucleic acid molecule comprising an anti-sense target sequence and a sequence complementary to the anti-sense target sequence, such that the molecule when single stranded and under appropriate conditions will form a hair pin structure, i.e., wherein anti-sense target sequence is hybridized to the complementary sequence. In some aspects, the molecule is an RNA molecule that can form a hair pin structure. In other aspects, the molecule is a DNA molecule that, when expressed as an RNA, can form a hair pin structure. For example, the anti-sense target sequence can be 22 nucleotides in length and the complementary sequence can be 22 nucleotides in length and can comprise 1 or 2 mismatches relative to the anti-sense target sequence.

Thus, in some embodiments, a recombinant nucleic acid molecule is provided comprising from 5' to 3' and in the order from (a)-(g): (a) a mir-16 flanking sequence (e.g., a flanking sequence from human MIR16-1 or MIR16-2); (b) a first lower stem sequence comprising a sequence from a mir-16 gene (e.g., a sequence from human MIR16-1 or MIR16-2); (c) an anti-sense target sequence 22 nucleotides in length; (d) a loop sequence comprising the sequence from a mir-30 gene (e.g., the human MIR30A gene); (e) a sense sequence wherein the sequence is complementary to the sequence of (c) except that the sequence comprises one or two mismatches relative to the sequence of (c); (f) a second lower stem sequence wherein the sequence is complementary to the sequence of (b); and (g) a second flanking sequence.

In some aspects, a recombinant nucleic acid sequence of the embodiments comprises (a) a mir-16 flanking sequence such as a sequence flanking the human MIR16-1 coding sequence (NCBI NR_029486, incorporated herein by reference). In some aspects, the mir-16 flanking sequence comprises 8, 9, 10, 11, 12, 13, 14, 15, 16, 17 or more nucleotides from a human MIR16 gene. For example, the sequence can comprise the sequence of SEQ ID NO: 1 or a sequence identical to SEQ ID NO: 1, but comprising 1, 2 or 3 nucleic acid deletions or substitutions. In certain aspects, the mir-16 flanking sequence consists of the sequence of SEQ ID NO: 1.

In further aspects, a recombinant nucleic acid sequence of the embodiments comprises (b) a first lower stem sequence comprising a sequence from a mir-16 such as from a human MIR16-1 gene. For example, the first lower stem sequence can comprises 8, 9, 10, 11, 12, 13, 14, 15, 16, 17, 18, 19 or 20 nucleotide from a human MIR16-1 gene sequence (e.g., a sequence comprising the 11 nucleotides of SEQ ID NO: 2). In certain aspects, the first lower stem sequence comprises a sequence of SEQ ID NO: 2, SEQ ID NO: 3, SEQ ID NO: 4, SEQ ID NO: 5 or SEQ ID NO: 6 or a sequence identical to any of the foregoing, but comprising 1, 2 or 3 nucleic acid deletions or substitutions. In some aspects, the first lower stem sequence consists of a sequence of SEQ ID NO: 2, SEQ ID NO: 3, SEQ ID NO: 4, SEQ ID NO: 5 or SEQ ID NO: 6.

In yet further aspects, a recombinant nucleic acid sequence of the embodiments comprises an antisense target sequence 22 nucleotides in length. As used herein an "anti-sense target sequence" refers to a nucleic acid sequence that is complementary to a gene encoding sequence from an organism, such as a mammal. For example, the sequence can be complementary to an exon of a mammalian target gene. In certain aspects, the anti-sense target sequence is complementary to a mRNA sequence (e.g., in the 5' UTR. 3' UTR or coding sequence of an mRNA). In still further aspects, the anti-sense target sequence is complementary to gene from a microorganism, such as a virus, bacteria or protozoa (e.g., *plasmodium*). Examples of mammalian genes that can be targeted include, without limitation, ribonucleotide reductase (e.g., the human M2 subunit), proprotein convertase subtilisin/kexin type 9 (PCSK9), transferrin receptor subtype 2 (TFR2), transthyretin (TITR), protein C, targeting transmembrane protease, serine 6 (Tmprss6), kinesin spindle protein (KSP), vascular endothelial growth factor (VEGF), chemokine receptor 5 (CCR5) and protein kinase N3 (PKN3). Non-limiting examples of viruses that can be targeted include, the genome or coding sequences from respiratory syncytial virus (RSV; e.g., the nucleocapsid gene of RSV), HIV, Ebola, dengue virus, influenza or herpes virus. Once a nucleic acid target sequence (e.g., a mRNA or viral genome) is selected a specific target sequence (complementary to the antisense target sequence) can be selected using techniques well established in the art (see e.g., the world wide web at broadinstitute.org/rnai/public/resources/rules). Additional non-limiting examples of genes that can be targeted by methods and constructs according the embodiments include bcr/abl fusions and PML/RaL alpha oncogenes (e.g., for anti-leukemia therapy).

In some aspects, a recombinant nucleic acid sequence of the embodiments comprises (d) a loop sequence, such as a mir-30 loop sequence. For example, the sequence can be a loop sequence from the human MIR30A gene (NCBI accession no. NR_029504; SEQ ID NO: 9). In further aspects, the loop sequence (d) comprises a fragment of 8, 9, 10, 11, 12, 13, 14, 15, 16, 17, 18, 19, 20, 21, 22, 23, 24 or 25 nucleotides of SEQ ID NO: 9 (e.g., a fragment including the sequence of SEQ ID NO: 7). Thus, in certain aspects, a loop sequence (d) comprises or consists of the sequence of SEQ ID NO: 7.

In still further aspects, recombinant nucleic acid sequence of the embodiments comprises (e) a sense sequence wherein the sequence is complementary to the anti-sense target sequence of (c) except that the sense sequence comprises one or two mismatches relative to the anti-sense target sequence (e.g., 1 or 2 nucleotides out of sequence of 22 nucleotides that are not complementary to the anti-sense target sequence). For example, a mismatch can be located at the position 8 to 14 of the sense sequence, such as at position 8, 9, 10, 11, 12, 13 or 14 of the sense sequence (e.g., at position 11). In further aspects, a mismatch can be located at the final 3' position (position 22) of the sense sequence. Thus, in some aspects, a recombinant nucleic acid of the embodiments comprises (i) a mismatch located at the position 8 to 14 of the sense sequence (e.g., at position 11) and (ii) a mismatch at the final 3' position (position 22) of the sense sequence.

In still a further aspect, a recombinant nucleic acid sequence of the embodiments comprises (f) a second lower stem sequence complementary to all or part of the first lower stem sequence (b). Thus, in some aspects, the second lower stem sequence comprises 8, 9, 10, 11, 12, 13, 14, 15, 16, 17, 18, 19 or 20 contiguous nucleotides complementary to the first stem loop sequence. Accordingly, in certain aspects, the second lower stem loop sequence comprises a sequence complementary to a mir-16 sequence such as a sequence from human MIR16-1 gene. For example, the second lower stem sequence can comprises 8, 9, 10, 11, 12, 13, 14, 15, 16, 17, 18, 19 or 20 nucleotides complementary to a human MIR16-1 gene sequence (e.g., a sequence complementary to the 11 nucleotides of SEQ ID NO: 2). In further aspects, the second lower stem sequence comprises a sequence complementary to SEQ ID NO: 2, SEQ ID NO: 3, SEQ ID NO: 4, SEQ ID NO: 5 or SEQ ID NO: 6. In some aspects, the second lower stem sequence consists of a sequence complementary to SEQ ID NO: 2, SEQ ID NO: 3. SEQ ID NO: 4, SEQ ID NO: 5 or SEQ ID NO: 6.

In still yet a further aspect, a recombinant nucleic acid sequence of the embodiments comprises a second flanking sequence (g) located 3' relative to the second lower stem loop sequence. In some aspects, the second flanking sequence can be 1, 2, 3, 4, 5, 6, 7, 8, 9, 10, 11, 12, 13, 14, 15, 20, 25, 30, 35, 40, 45, 50 or more nucleotides in length. In some cases, the second flanking sequence is a sequence from a human micro RNA (MIR) gene. For example, the sequence can be from the 3' flanking sequence (i.e., a sequence located 3' of the encoded RNA stem-loop) of a MIR gene. In some preferred aspects, the second flanking sequence is not from a mir-16 gene or is not complementary to the mir-16 flanking sequence (a).

As indicated above, in some aspects, a recombinant nucleic acid of the embodiments is a DNA or an RNA molecule. In still further aspects, the molecule can be composed of one or more nucleotide position comprising a C5-ethynyl locked nucleic acid (LNA), cyclohexenyl nucleic acid (CeNA), anhydrohexital nucleic acid (HNA), or threofuranosyl nucleid acid (TNA). In some aspects, the recombinant nucleic acid is a DNA molecule such a DNA sequence comprised in a plasmid or expression vector. For example, expression vectors are provided that comprise expression control sequences operably linked to a recombinant nucleic acid of the embodiments thereby providing expression of an RNA molecule in accordance with the present embodiments. In some aspects, an expression vector comprises a promoter (e.g., a eukaryotic Pol I, Pol II or Pol III promoter), an intron, an enhancer, a poly-A signal, sequence and/or a transcription terminator sequence. Non-limiting examples of promoters for use according to the embodiments include inducible (e.g., drug inducible or repressible promoters), constitutive, tissue-specific, cell-type specific, cell lineage-specific and circadian promoters. Examples of expression vectors for use according to the embodiments include, without limitation, plasmids, episomal vectors, adenoviral vectors, adeno-associated viral vectors, retroviral vectors, lentiviral vectors (e.g., HIV-based vectors) and pox virus vectors.

In still further aspects, an expression vector in accordance with the embodiments further encodes one or more additional genetic elements. Examples, of additional genetic elements that can be comprised in an expression vector include, without limitation, drug resistance or sensitivity markers, reporter genes (e.g., encoding a fluorescence protein) or therapeutic genes.

In certain aspects, a nucleic acid molecule of the embodiments comprises two or more repeats of the sequences provided herein. For example, the molecules can comprise at least 2, 3, 4, 5, 6 or more repeats of the sequences (a)-(g). In some aspects, such repeats are separated by a spacer sequence. In the case of an expression vector, repeat sequences may be expressed from a common promoter or may be under the control of two or more different promoters. Thus, in certain aspects, 2 or more copies of a nucleic acid sequence of the embodiments form a polycistronic transcript.

In a further embodiment there is provided a host cell comprising a recombinant nucleic acid molecule of the embodiments. For example, the host cell can be a prokaryotic or eukaryotic host cell, such as a mammalian cell. In some cases, the host cell comprises an expression vector of the embodiments. Host cells for instance can be transiently transfected with the nucleic acid or may comprise a stable expression vector (e.g., a genome integrated or episomal vector). In certain aspects the host cell is a stem cell (e.g., an induced pluripotent stem (iPS) cell), a cell from a transformed cell line or a primary cell, such as a primary blood cell. In specific aspects, the host cell is a CD4 positive T cell or a macrophage.

In yet a further embodiment a method is provided for reducing expression of a gene in a cell comprising expressing a nucleic acid molecule of the embodiments in the cell wherein the anti-sense target sequence (c) is complementary to the sense strand of the gene. In further aspects, a method is provided for reducing expression of a gene in a cell comprising (i) obtaining a nucleic acid molecule of the embodiments that comprises an anti-sense target sequence (c) complementary to the sense strand of the gene; and (ii) expressing the nucleic acid molecule so obtained in the cell. For example, a nucleic acid of the embodiments can be introduced into a cell (e.g., transfected) as an RNA or DNA (e.g., an expression vector). In some aspects, the cell is in culture (e.g., in vitro or ex vivo) in other aspects the cell is in an organism (an in vivo method).

In some aspects, a method of the embodiments further comprises selecting or isolating a cell expressing a nucleic acid molecule of the embodiments. For instance, a cell expressing the nucleic acid can be selected by detecting expression of the nucleic acid molecule or expression of a reporter gene. In further aspects, a cell comprising the nucleic acid can be selected using a drug selection (i.e., wherein the nucleic acid molecule includes a drug selection marker).

In still further aspects, a method can comprise transplanting a cell expressing the nucleic acid molecule into an organism, such as a human. In some cases, a selection for cells expressing a nucleic acid molecule can be in vivo, such as by administering an effective amount of a selection drug to an organism comprising the cells.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Invention

Figure 1:
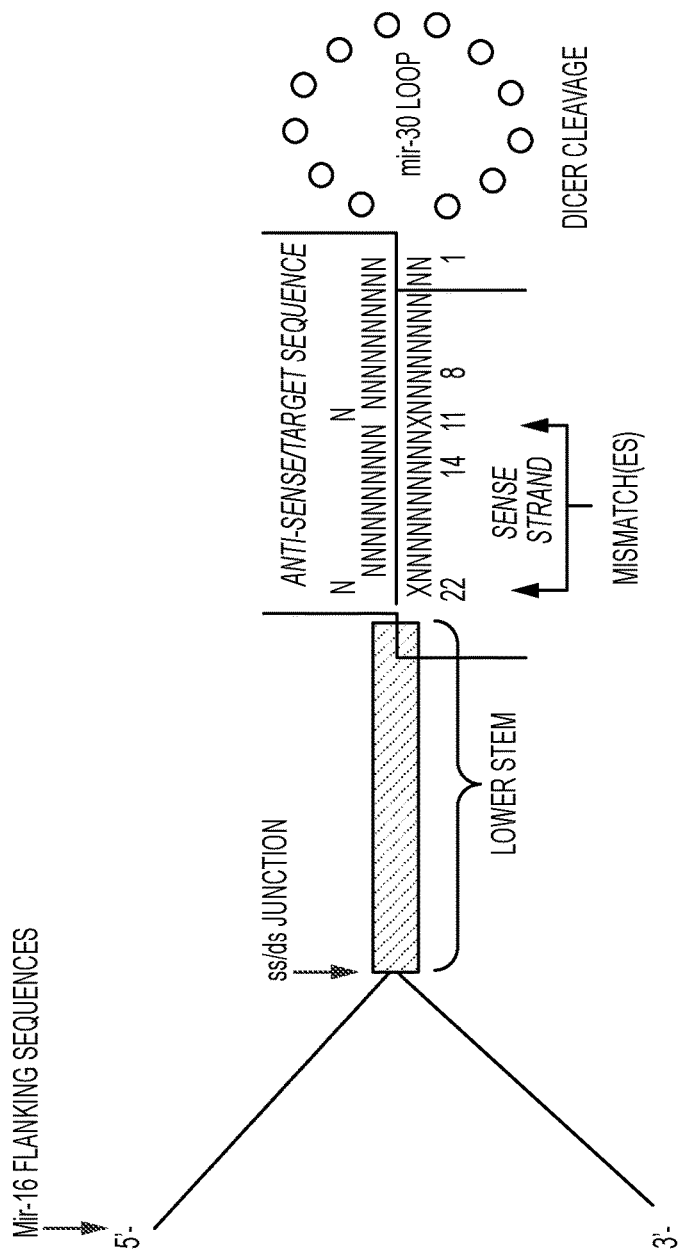
FIG. 1: Figure shows a schematic representation of an example recombinant nucleic acid molecules of the embodiments. Numbering indicates the nucleic acid positions relative to the sense sequence (which is partially complementary to the anti-sense target sequence).

RNAi has the potential to provide sequence-specific down-regulation of gene expression. Such specific regulation would be useful in treating a wide range of genetic disorders and in combating infectious diseases. However, a major problem to date with such therapies is that the knock-down of gene expression is insufficient to provide significant practical clinical benefit. It has previously been unclear how, or if, this problem could be effectively addressed.

Studies presented here demonstrate a new design for molecules that mediate knock-down of gene expression. The new molecules are able to suppress target gene expression to a very low level that was not previously achievable, particularly at low levels of transduction. Specifically, studies presented here show down-regulation of CCR5 gene expression, an important HIV co-receptor critically involved in the process of host cell infection. The studies employ modified HeLa cells that stably express human CCR5 at a level significantly higher as compared to native immune cells. Upon expression of the newly designed RNA molecules the efficiency of CCR5 down-regulation is increased by 100% as compared to previously available targeted RNA expression vectors. Importantly, this highly improved down-regulation was analyzed in test samples where the level of transduction is carefully controlled and samples where only 2-20% of the population are transduced, such that a single lentivector copy per cell was used for analysis. Cells transduced with this new generation lentivector at multiple or several copies per cell were stained with DAPI after being kept in culture for over two weeks, and the staining revealed that the cells were not showing any signs of cytotoxicity due to the insertion of the RNA expression cassettes by the lentivector.

Gene therapy approaches for curing genetic as well as many other possible diseases would be ideal as a way to eliminate the need for lifelong or even long term drug regimens often leading to adverse drug related effects. However, many such gene therapy approaches would require a single "dose" or gene therapy procedure resulting in lifelong immunity to some of the most important diseases of our time. The molecules detailed herein for the first time offer robust knock-down of gene expression even when the molecules are delivered to cells in single copy. This is of particular advantage since, for example, in the case of lentiviral vectors, multiple integration copies should be avoided to reduce the risk of disrupting an essential gene in the cell or activating an oncogene. Thus, the molecules detailed here will be of great use in new genetic approaches to disease treatment. ps II. Vectors for Cloning, Gene Transfer and Expression Within certain aspects expression vectors are employed to express a nucleic acid of interest, such as a nucleic acid that inhibits the expression of a particular gene. Expression requires that appropriate signals be provided in the vectors, and which include various regulatory elements, such as enhancers/promoters from both viral and mammalian sources that drive expression of the genes of interest in host cells. Elements designed to optimize RNA stability in host cells also are defined. The conditions for the use of a number of dominant drug selection markers for establishing permanent, stable cell clones expressing the products are also provided, as is an element that links expression of the drug selection markers to expression of the polypeptide.

A. Regulatory Elements

Throughout this application, the term "expression construct" or "expression vector" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest i.e., as is the case with RNA molecules of the embodiments.

In certain embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for eukaryotic RNA polymerase (Pol) I, II or III. Much of the thinking about how promoters are organized derives from analyses of several viral Pol II promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In other embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several regulatory elements that may be employed, in the context of the present invention, to regulate the expression of the gene of interest. This list is not intended to be exhaustive of all the possible elements involved in the promotion of gene expression but, merely, to be exemplary thereof. In some aspects, a promoter for use according to the instant embodiments is a non-tissue specific promoter, such as a constitutive promoter.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α₁-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |

TABLE 2-continued

Promoter and/or Enhancer

| Promoter/Enhancer | References |
|---|---|
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, and more particularly, cardiac specific promoters. These include the myosin light chain-2 promoter (Franz et al., 1994; Kelly et al., 1995), the alpha actin promoter (Moss et al., 1996), the troponin 1 promoter (Bhavsar et al., 1996); the Na$^+$/Ca$^{2+}$ exchanger promoter (Barnes et al., 1997), the dystrophin promoter (Kimura et al., 1997), the alpha7 integrin promoter (Ziober and Kramer, 1996), the brain natriuretic peptide promoter (LaPointe et al., 1996) and the alpha B-crystallinismall heat shock protein promoter (Gopal-Srivastava, 1995), alpha myosin heavy chain promoter (Yamauchi-Takihara el al., 1989) and the ANF promoter (LaPointe et al., 1988).

Where any cDNA insert is employed, one will typically include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. In some aspects, however, a polyadenylation signal sequence is not included in a vector of the embodiments. For example, incorporation of such a signal sequence in lentiviral vectors (before a 3' LTR) can reduce resulting lentiviral titers.

Also contemplated as an element of the expression cassette is a terminator. These elements can serve to enhance message levels and to minimize read through from the cassette into other sequences.

B. Selectable Markers

In certain embodiments of the invention, the cells contain nucleic acid constructs of the present invention, a cell may be identified in vitro, ex vivo or in viv, by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR. GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

III. Delivery of Nucleic Acid Molecules and Expression Vectors

In certain aspects, vectors for delivery of nucleic acids of the embodiments could be constructed to express these factors in cells. In a particular aspect, the following systems and methods may be used in delivery of nucleic acids to desired cell types.

A. Homologous Recombination

In certain aspects of the embodiments, the vectors encoding nucleic acid molecules of the embodiments may be introduced into cells in a specific manner, for example, via homologous recombination. Current approaches to express genes in stem cells have involved the use of viral vectors (e.g., lentiviral vectors) or transgenes that integrate randomly in the genome. These approaches have not been successful due in part because the randomly integrated vectors can activate or suppress endogenous gene expression, and/or the silencing of transgene expression. The problems associated with random integration could be partially overcome by homologous recombination to a specific locus in the target genome.

Homologous recombination (HR), also known as general recombination, is a type of genetic recombination used in all forms of life in which nucleotide sequences are exchanged between two similar or identical strands of DNA. The technique has been the standard method for genome engineering in mammalian cells since the mid 1980s. The process involves several steps of physical breaking and the eventual rejoining of DNA. This process is most widely used in nature to repair potentially lethal double-strand breaks in DNA. In addition, homologous recombination produces new combinations of DNA sequences during meiosis, the process by which eukaryotes make germ cells like sperm and ova. These new combinations of DNA represent genetic variation in offspring which allow populations to evolutionarily adapt to changing environmental conditions over time. Homologous recombination is also used in horizontal gene transfer to exchange genetic material between different strains and species of bacteria and viruses. Homologous recombination is also used as a technique in molecular biology for introducing genetic changes into target organisms.

Homologous recombination can be used as targeted genome modification. The efficiency of standard HR in mammalian cells is only $10^{-6}$ to $10^{-9}$ of cells treated (Capecchi, 1990). The use of meganucleases, or homing endonucleases, such as I-SceI have been used to increase the efficiency of HR. Both natural meganucleases as well as engineered meganucleases with modified targeting specificities have been utilized to increase HR efficiency (Pingoud and Silva, 2007; Chevalier et al., 2002). Another path toward increasing the efficiency of HR has been to engineer chimeric endonucleases with programmable DNA specificity domains (Silva et al., 2011). Zinc-finger nucleases (ZFN) are one example of such a chimeric molecule in which Zincfinger DNA binding domains are fused with the catalytic domain of a Type IIS restriction endonuclease such as FokI (as reviewed in Durai et al., 2005; PCT/US2004/030606). Another class of such specificity molecules includes Transcription Activator Like Effector (TALE) DNA binding domains fused to the catalytic domain of a Type IIS restriction endonuclease such as FokI (Miller et al., 2011: PCT/IB2010/000154).

B. Nucleic Acid Delivery Systems

One of skill in the art would be well equipped to construct a vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g., derived from Moloney murine leukemia virus vectors (MoMLV), MSCV, SFFV, MPSV, SNV etc), lentiviral vectors (e.g., derived from HIV-1. HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

1. Episomal Vectors

The use of plasmid- or liposome-based extra-chromosomal (i.e., episomal) vectors may be also provided in certain aspects of the invention, for example, for reprogramming of somatic cells. Such episomal vectors may include, e.g., oriP-based vectors, and/or vectors encoding a derivative of EBV-protein EBNA-1. These vectors may permit large fragments of DNA to be introduced to a cell and maintained extra-chromosomally, replicated once per cell cycle, partitioned to daughter cells efficiently, and elicit substantially no immune response.

In particular. EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Also other sources of episome-based vectors are contemplated, such as yeast ARS, adenovirus. SV40, or BPV.

One of skill in the art would be well equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also might include markers, such as detectable and/or selection markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

2. Transposon-Based System

According to a particular embodiment the introduction of nucleic acids may use a transposon-transposase system. The used transposon—transposase system could be the well known Sleeping Beauty, the Frog Prince transposon—transposase system (for the description of the latter see e.g., EP1507865), or the TTAA-specific transposon piggyback system.

Transposons are sequences of DNA that can move around to different positions within the genome of a single cell, a process called transposition. In the process, they can cause mutations and change the amount of DNA in the genome. Transposons were also once called jumping genes, and are examples of mobile genetic elements.

There are a variety of mobile genetic elements, and they can be grouped based on their mechanism of transposition. Class I mobile genetic elements, or retrotransposons, copy themselves by first being transcribed to RNA, then reverse transcribed back to DNA by reverse transcriptase, and then being inserted at another position in the genome. Class II mobile genetic elements move directly from one position to another using a transposase to "cut and paste" them within the genome.

3. Viral Vectors

In generating recombinant viral vectors, non-essential genes are typically replaced with a gene or coding sequence for a heterologous (or non-native) protein or nucleic acid. Viral vectors are a kind of expression construct that utilizes viral sequences to introduce nucleic acid and possibly proteins into a cell. The ability of certain viruses to infect cells or enter cells via pH-dependent or pH-independent mechanisms, to integrate their genetic cargo into a host cell genome and to express viral genes stably and efficiently have made them attractive candidates for the transfer of foreign nucleic acids into cells (e.g., mammalian cells). Non-limiting examples of virus vectors that may be used to deliver a nucleic acid of certain aspects of the present invention are described below.

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid (i.e., the vector genome) to be packaged into viral particles, which are then secreted into the culture media (Nicolas and Rubenstein, 1988: Temin. 1986; Mann et al., 1983). The media containing the recombinant retroviruses is then collected, optionally concentrated, and used for gene transfer. Depending on the tropism of the envelope protein used to cover the vector particles surface, retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zuffercy et al., 1997; Blomer et al., 1997; Giry-Laterriere et al., 2011; U.S. Pat. Nos. 6,013,516 and 5,994.136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference.

C. Nucleic Acid Delivery

Introduction of a nucleic acid, such as DNA or RNA, into cells to be programmed with the current invention may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981.274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

1. Liposome-Mediated Transfection

In a certain embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen). The amount of liposomes used may vary upon the nature of the liposome as well as the cell used, for example, about 5 to about 20 µg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong el al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

2. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 µg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

3. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

4. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

D. Cell Culturing

Generally, cells of the present invention are cultured in a culture medium, which is a nutrient-rich buffered solution capable of sustaining cell growth.

Culture media suitable for isolating, expanding and differentiating stem cells according to the method described herein include but not limited to high glucose Dulbecco's Modified Eagle's Medium (DMEM), DMEMJF-12, Liebovitz L-15, RPMI 1640, Iscove's modified Dubelcco's media (IMDM), and Opti-MEM SFM (Invitrogen Inc.). Chemically Defined Medium comprises a minimum essential medium such as Iscove's Modified Dulbecco's Medium (IMDM) (Gibco), supplemented with human serum albumin, human Ex Cyte lipoprotein, transferrin, insulin, vitamins, essential and non essential amino acids, sodium pyruvate, glutamine and a mitogen is also suitable. As used herein, a mitogen refers to an agent that stimulates cell division of a cell. An agent can be a chemical, usually some form of a protein that encourages a cell to commence cell division, triggering mitosis. In one embodiment, serum free media such as those described in U.S. Ser. No. 08/464,599 and WO96/39487, and the "complete media" as described in U.S. Pat. No. 5,486,359 are contemplated for use with the method described herein. In some embodiments, the culture medium is supplemented with 10% Fetal Bovine Serum (FBS), human autologous serum, human AB serum or platelet rich plasma supplemented with heparin (2 U/ml). Cell cultures may be maintained in a $CO_2$ atmosphere, e.g., 5% to 12%, to maintain pH of the culture fluid, incubated at 37° C. in a humid atmosphere and passaged to maintain a confluence below 85%.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Vector Construction of New Generation Mir-16 Lentivectors

Artificial CCR5 targeting miRNA oligos were generated by PCR using the following primers:

```
FW:
CAGAAGGGGATCCATCGATACTAGTGGTGATAGCAATGT
CAGCAGTGCCT

REV:
5'-AGTAGCTTCTAGAGTAGAGTATGGTCAACCTTACTT
```

The Herculase II Fusion DNA Polymerase was used for the PCR reaction. Reaction conditions were set up according to the manufacturers specifications (Agilent technologies, Santa Clara, USA). The PCR products were digested with BamHI and XbaI restriction enzymes (New England Biolabs, Ipswich, Mass.), and ligated into a pENTR Gateway entry plasmid already containing the Green fluorescent protein (GFP) coding sequence, pENTR-GFP cut BamHI, XbaI. The digested miRNA oligo was ligated into the pENTR-GFP using T4 DNA ligase concentrated (New England Biolabs, Ipswich, Mass.). pENTR-GFP constructs with multiple miRNAs were created by a method adapted from (Sun et al., 2006). The final lentivector with the human UBI promoter driving expression of GFP and the miRNAs were constructed by carrying out a Gateway LR reaction with HIV-1 derived 3rd generation lentivector backbone, pCLX.

EXAMPLE 2

Virus Production and Titration

Lentiviral vector stocks were generated using the HIV-1 derived packaging psPAX2 and envelope pCAG-VSVG plasmids using by calcium phosphate mediated transient transfection of HEK 293T cells, a method previously described (Salmon & Trono 2007). Lentiviral titer was assessed via flow cytometry by analyzing the level of reporter gene (GFP) in transduced HeLa cells after 5 days, as described previously (Giry-Laterriere el al., 2011; Salmon and Trono, 2011) on a facscalibur.

EXAMPLE 3

Transduction of Target Cells and CCR5 Knockdown Analysis

In order to test the knockdown effect of the new generation mir-16 miRNA lentiviral vector, a modified HeLa cell line (TZ) cells were used that express native CCR5 protein. TZ cells cultured in DMEM were transduced with 3 different volumes of harvested lentivector. After 5 days cells were stained with an APC labeled monoclonal human CCR5 antibody (BD Biosciences) (as a control non-CCR5 expressing HeLa were used) and transduction efficiency was analyzed by measuring the level of GFP expression by flow cytometry. Samples where between 2-20% of the cells were transduced (expressed GFP) were used for further analysis which allows us to look at the knockdown effect of the various lentivector constructs at a level of 1 copy per cell.

EXAMPLE 4

Results and Discussion

Figure 2A:
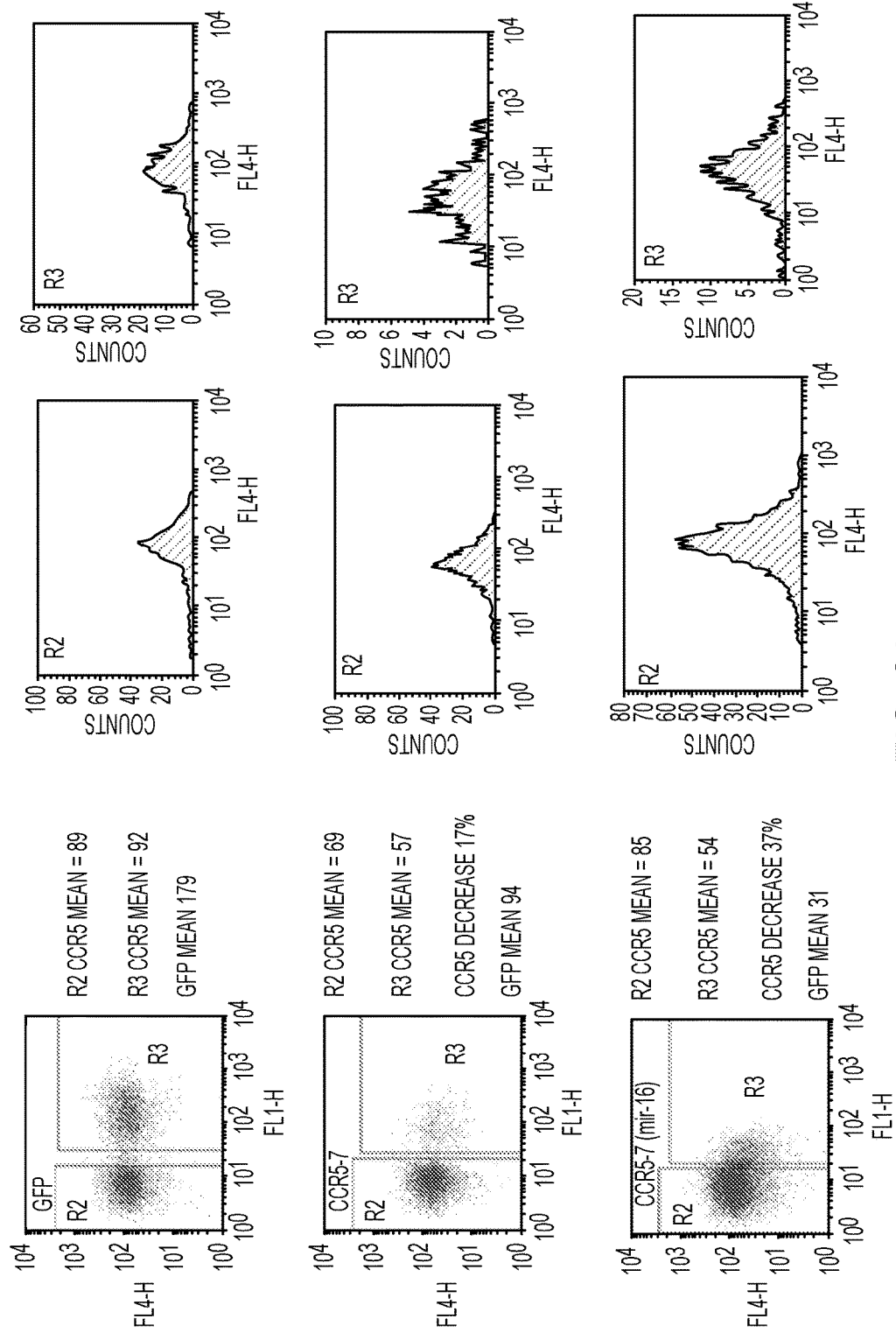
FIG. 2A-C: Flow cytometry analysis of various CCR5 knockdown lentivector constructs. The scatter plots on the left show on the X axis (horizontal axis) level of GFP fluorescence. The Y axis (vertical axis) is level of CCR5 fluorescence. The first log decade on both axes is negative. Each scatter plot is a single lentivector construct and shows two distinct populations R2 (untransduced) and R3 (transduced). The control sample (GFP) is a simple GFP only lentivector with no CCR5 knockdown. (CCR5-7) is a lentivector expressing GFP as well as the old mir-30 based CCR5 targeting miRNA, where 7 is the label of target sequence arbitrarily labeled 7. (CCR5-7-7) indicates a lentivector with 2 mir-30 based miRNAs. (CCR5-7 mir-16) designates the lentivectors containing the new generation of hybrid miRNAs. The GFP mean value in green is the GFP mean of the transduced population in each case R3.
Figure 2B:
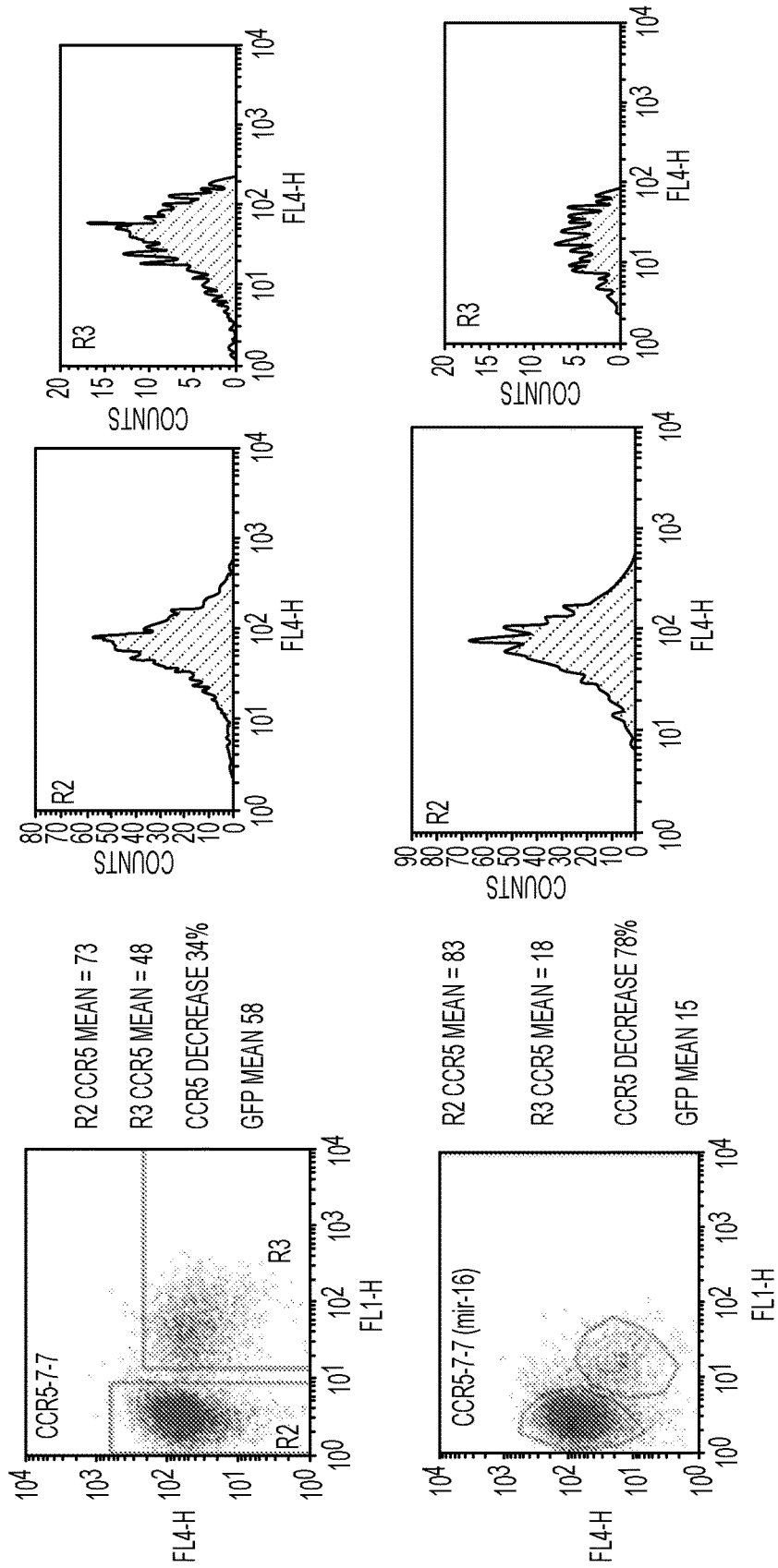
Figure 2C:
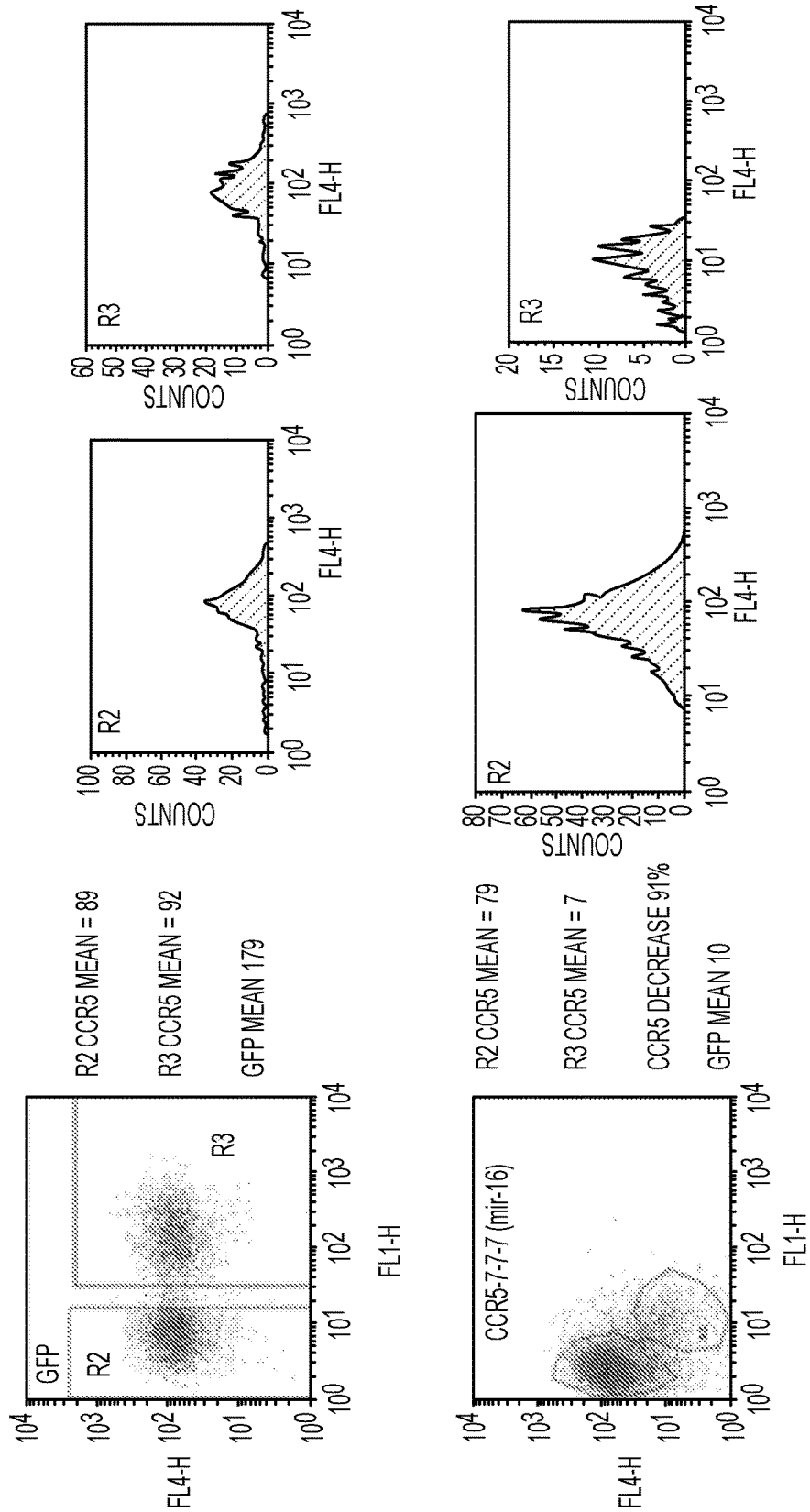

Flow cytometry analysis was performed using various CCR5 knockdown lentivector constructs (FIG. 2A-C). The scatter plots on the left showed on the X axis (horizontal axis) level of GFP fluorescence. The Y axis (vertical axis) is level of CCR5 fluorescence. The first decade on both axes is negative. Each scatter plot is a single lentivector construct and shows two distinct populations R2 (untransduced) and R3 (transduced). The control sample (GFP) is a simple GFP only lentivector with no CCR5 knockdown. (CCR5-7) is a lentivector expressing GFP as well as the old mir-30 based CCR5 targeting miRNA, where 7 is the label of target sequence arbitrarily labeled 7. (CCR5-7-7) indicates a lentivector with 2 mir-30 based miRNAs. (CCR5-7 mir-16) designates the lentivectors containing the new generation of hybrid miRNAs. The GFP mean value in green is the GFP mean of the transduced population in each case R3.

Figure 3:
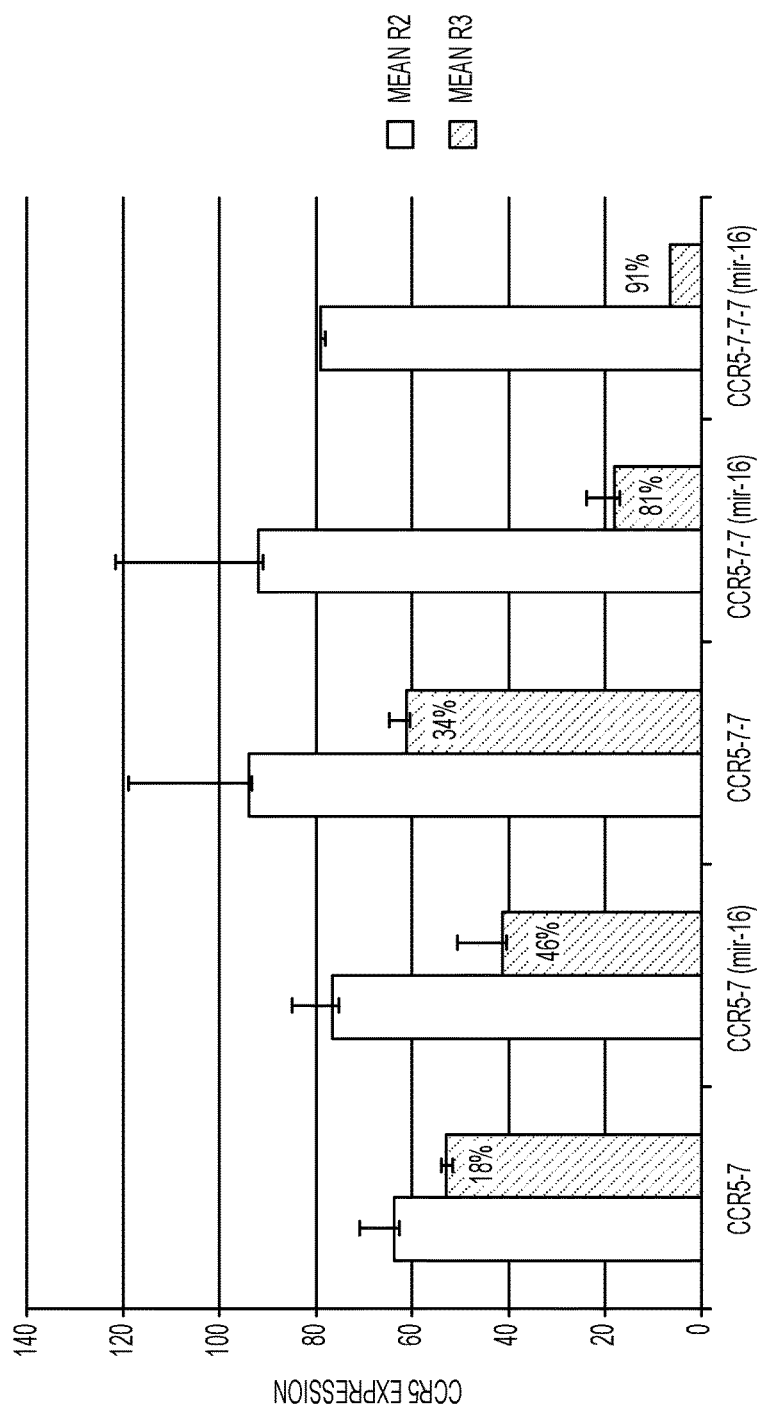
FIG. 3: CCR5 knockdown results were determined by flow cytometry as described in the examples and the results were graphed. R2 CCR5 expression and R3 CCR5 expression are shown as average mean fluorescence value of several experiments with standard deviation indicated. R3 CCR5 knockdown shown as a percentage as compared to R2 of each individual miRNA. Knockdown effect between CCR5-7 vs. CCR5-7 (mir-16) & CCR5-7-7 vs. CCR5-7-7 (mir-16) in both cases efficiency is improved more than 100% (i.e., more than double the knockdown effect is observed).

The current studies were based on pri-miRNA molecules employing the widely used human mir-30 backbone (Sun et al., 2006). As described above this resulted in a generally weak down-regulation of the target gene. Employing a polycistronic mir-30 based system did indeed yield improved results, however a saturation point was reached, meaning after a certain point, increasing the number of pri-miRNAs does not increase the knockdown effect. The next phase of the work was to completely redesign the backbone of our pri-miRNA molecule, not basing this new design on any particular or single naturally occurring human pri-miRNA backbone. The goal of this new design was to ensure the pri-miRNA transcript is efficiently incorporated into the RNAi pathway and smoothly processed to produce a stronger down-regulation effect. The result of this new hybrid design was a 100% increase in down-regulation efficiency as compared to the original human mir-30 based design (FIG. 3). This result was achieved over several experiments at varying copy number per cell of lentiviral vector (varying MOT). The new design always produced just over double the knockdown as compared to the old mir-30 based design. This can most likely be attributed to a superior processing of the new design, more readily producing miRNA duplexes which were designed to, after their processing, ensure better incorporation of the correct strand into the RISC complex.

Another aspect of the data to consider is the X axis mean of the R3 population or transduced population. Due to the way the lentivector is constructed the GFP and miRNA are transcribed as one transcription unit which means that the miRNAs are situated at the terminal end of the GFP transcript. The implications of this is that if the miRNAs are easily and efficiently recognized and processed by Drosha in the nucleus they will be separated from the terminal end of the GFP transcript, leaving the GFP mRNA with no poly A tail. This significantly affects the stability/translation of the GFP transcript and is detectable in a decrease in the mean GFP value of the transduced population as compared to the untransduced population in each sample. Indeed superior processing of the new (mir-16) design was observed compared to the old design is evident in the large difference between the transduced populations R3 X mean (GFP)

values, for example the mean GFP of R3 in the GFP only lentivector is 179, this can be used as a base GFP level. It is important to note that in the GFP only lentivector the CCR5 level stays the same between the R2 and R3 populations. If the GFP mean of R3 is observed in the single miRNA (old design construct), it has decreased from 179 to 94 indicating that some of the GFP fluorescence has been lost which means some miRNA has been recognized and processed. This is supported by accompanied 17% decrease in CCR5 expression. However in the single miRNA new design construct GFP mean in R3 has decreased to 31 which should mean that more of the miRNAs have been recognized and processed and therefore more down-regulation is achieved (which is there a 37% decrease in CCR5 fluorescence, more than double the effect as compared to the old design). This is a trend seen throughout several transduction experiments with varying number of miRNAs per construct. The general trend is between a single and double construct new and old design if you go from a single to double miRNA the down-regulation is doubled, 7 (old)=17% vs. 7-7 (old)=34%; 7 (mir-16)=37% vs. 7-7 (mir-16)=78%. However if one compares just the single miRNAs 7 (old)=17% vs. 7 (mir-16) new design=37%, the new single miRNA always gives double the effect of the old design. This is the same for the double constructs, 7-7 (old)=34% vs. 7-7 (mir-16)=78%. However when you add a triple hairpin you do not have double the effect again you have less, indicating that a pathway saturation point is being reached, 7-7 (mir-16)=78% vs. 7-7-7 (mir-16)=91%.

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,302,523
U.S. Pat. No. 5,322,783
U.S. Pat. No. 5,384,253
U.S. Pat. No. 5,464,765
U.S. Pat. No. 5,486,359
U.S. Pat. No. 5,538,877
U.S. Pat. No. 5,538,880
U.S. Pat. No. 5,550,318
U.S. Pat. No. 5,563,055
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,945,100
U.S. Pat. No. 5,981,274
U.S. Pat. No. 5,994,136
U.S. Pat. No. 5,994,136
U.S. Pat. No. 5,994,624
U.S. Pat. No. 6,013,516
U.S. Ser. No. 08/464,599
Angel et al., *Cell*, 49:729, 1987a.
Angel et al., *Cell*, 49:729, 1987b.
Atchison and Perry, *Cell*, 46:253, 1986.
Atchison and Perry, *Cell*, 48:121, 1987.
Ausubel et al., *Current Protocols in Molecular Biology*, Greene Publishing Associates and Wiley Interscience, N.Y., 1994.
Ausubel et al., *Current Protocols in Molecular Biology*, Greene Publishing Associates and Wiley Interscience, N.Y., 1996.
Banerji et al., *Cell*, 27:299, 1981.
Banerji et al., *Cell*, 33(3):729-740, 1983.
Barnes et al., *J. Biol. Chem.*, 272(17):11510-11517, 1997.
Berkhout et al., *Cell*, 59:273-282, 1989.
Bhavsar et al., *Genomics*, 35(1): 11-23, 1996.
Blanar et al., *EMBO J.*, 8:1139, 1989.
Blomer et al., *J. Virol.*, 71(9):6641-6649, 1997.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Bulla and Siddiqui, *J. Virol.* 62:1437, 1986.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Capecchi, *Nature*, 348(6297):109, 1990.
Celander and Haseltine, *J. Virology*, 61:269, 1987.
Celander et al., *J. Virology*, 62:1314, 1988.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell Biol.*, 7(8):2745-2752, 1987.
Chevalier et al., *Molec. Cell*, 10:895-905, 2002.
Choi et al., *J. Mol. Biol.*, 262(2):151-167, 1996.
Cohen et al., *J. Cell. Physiol.*, 5:75, 1987.
Costa et al., *Mol. Cell. Biol.*, 8:81-90, 1988.
Cripe et al., *EMBO J.*, 6:3745, 1987.
Culotta and Hamer, *Mol. Cell. Biol.*, 9:1376-1380, 1989.
Dandolo et al., *J. Virology*, 47:55-64, 1983.
Deschamps et al., *Science*, 230:1174-1177, 1985.
Durai et al., *Nucleic Acids Res.*, 33(18):5978-5990, 2005.
Edbrooke et al., *Mol. Cell. Biol.*, 9:1908-1916, 1989.
Edlund et al., *Science*, 230:912-916, 1985.
European Appln. EP 1507865
Evans et al., In: *Cancer Principles and Practice of Oncology*, Devita et al. (Eds.), Lippincot-Raven. NY, 1054-1087, 1997.
Fechheimer et al., *Proc. Natl. Acad. Sci. USA*, 84:8463-8467, 1987.
Feng and Holland, *Nature*, 334:6178, 1988.
Firak and Subramanian, *Mol. Cell. Biol.*, 6:3667, 1986.
Foecking and Hofstetter, *Gene*. 45(1):101-105, 1986.
Fraley et al., *Proc. Natl. Acad. Sci. USA*, 76:3348-3352, 1979.

Franz et al., *Cardioscience*, 5(4):235-43, 1994.
Fujita et al., *Cell*, 49:357, 1987.
Ghosh and Bachhawat. In: *Liver Diseases, Targeted Diagnosis and Therapy Using Specific Receptors and Ligands*, Wu et al. (Eds.), Marcel Dekker, NY, 87-104, 1991.
Gillies et al., *Cell*, 33:717, 1983.
Giry-Laterriere et al., *Methods in Mol. Biol.*, 737:183-209, 2011.
Gloss et al., *EMBO J.*, 6:3735, 1987.
Godbout et al., *Mol. Cell. Biol.*, 8:1169, 1988.
Goodbourn and Maniatis, *Cell*, 41(2):509-520, 1985.
Goodbourn et al., *Cell*. 45:601, 1986.
Gopal, Mol. Cell *Biol.*, 5:1188-1190, 1985.
Gopal-Srivastava et al., *J. Mol. Cell. Biol.* 15(12):7081-7090, 1995.
Graham and Van Der Eb, *Virology*, 52:456-467, 1973.
Greene et al., *Immunology Todlay*, 10:272, 1989.
Grosschedl and Baltimore, *Cell*, 41:885, 1985.
Harland and Weintraub, *J. Cell Biol.*, 101(3):1094-1099, 1985.
Haslinger and Karin. *Proc. Natl. Acad. Sci. USA*, 82:8572, 1985.
Hauber and Cullen, *J. Virology*, 62:673, 1988.
He and Hannon, *Nat. Rev. Genet.*, 5:522-531, 2004.
Hen et al., *Nature*. 321:249, 1986.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Huang et al., *Cell*, 27:245, 1981.
Hug et al., *Mol. Cell. Biol.*, 8:3065-3079, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9(8):3393-3399, 1989.
Kadesch and Berg, *Mol. Cell. Biol.*, 6:2593, 1986.
Kaeppler et al., *Plant Cell Rep.*, 9:415-418, 1990.
Kaneda et al., *Science*, 243:375-378, 1989.
Karin et al., *Mol. Cell. Biol.*, 7:606, 1987.
Karin et al., *Mol. Cell. Biol.*, 7:606, 1987.
Katinka et al., *Cell*, 20:393, 1980.
Katinka et al., *Nature*, 290:720, 1981.
Kato et al, *J. Biol. Chem.*, 266:3361-3364, 1991.
Kawamoto et al., *Mol. Cell. Biol.*, 8:267, 1988.
Kelly et al., *J. Cell Biol.*, 129(2):383-396, 1995.
Kiledjian et al., *Mol. Cell. Biol.*, 8:145, 1988.
Kimura et al., *Dev. Growth Differ.* 39(3):257-265, 1997.
Klamut et al., *Mol. Cell. Biol.*, 10:193, 1990.
Koch et al., *MAol. Cell. Biol.*, 9:303, 1989.
Krieglcr and Botchan, *Mol. Cell. Biol.*, 3:325, 1983.
Kriegler et al., *Cell*, 38:483, 1984a.
Kriegler et al., In: *Cancer Cells 2/Oncogenes and Viral Genes*, Van de Woude et al. eds, Cold Spring Harbor, Cold Spring Harbor Laboratory, 1984b.
Kuhl et al., *Cell*. 50:1057, 1987.
Kunz et al., *Nucl. Acids Res.*, 17:1121, 1989.
Langle-Rouault et al., *J. Virol.*, 72(7):6181-6185, 1998.
LaPointe et al., *Hypertension* 27(3 Pt 2):715-22, 1996.
LaPointe et al., *J. Biol. Chem.*, 263(19):9075-9078, 1988.
Larsen et al., *Proc. Natl. Acad. Sci. USA*, 83:8283, 1986.
Laspia et al., *Cell*, 59:283, 1989.
Latimer et al., *Mol. Cell. Biol.*, 10:760, 1990.
Lee et al., *Nature*, 294:228, 1981.
Lee et al., *Nucleic Acids Res.*, 12:4191-206, 1984.
Levitskaya et al., *Proc. Natl. Acad. Sci. USA*, 94(23):12616-12621, 1997.
Lin et al., *Mol. Cell. Biol.*, 10:850, 1990.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Majors and Varmus, *Proc. Natl. Acad. Sci. USA*, 80:5866, 1983.
Maniatis, et al., Molecular Cloning, A Laboratory Manual, Cold Spring Harbor Press, Cold Spring Harbor, N.Y., 1988.
Mann et al., *Cell*, 33:153-159, 1983.
McNeall et al., *Gene*. 76:81, 1989.
Miksicek et al., *Cell*, 46:203, 1986.
Miller et al., *Am. J. Clin. Oncol.*, 15(3):216-221, 1992.
Mordacq and Linzer, *Genes and Dev.*, 3:760, 1989.
Moreau et al., *Nucl. Acids Res.*, 9:6047, 1981.
Moss et al., *Biol. Chem.*, 271(49):31688-31694, 1996.
Muesing et al., *Cell*, 48:691, 1987.
Nabel et al., *Science*. 244(4910): 1342-1344, 1989.
Naldini et al., *Science*, 272(5259):263-267, 1996.
Neuberger et al., *Nucleic Acids Res.*, 16(14B):6713-6724, 1988.
Ng et al., *Nuc. Acids Res.*, 17:601, 1989.
Nicolas and Rubenstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Omitz et al., *Mol. Cell. Biol.*, 7:3466, 1987.
Ondek et al., *EMBO J.* 6:1017, 1987.
Palmiter et al., *Cell*, 29:701, 1982.
Paskind et al., *Virology*, 67:242-248, 1975.
PCT Appln. PCT/IB2010/000154
PCT Appln. PCT/US2004/030606
PCT Appln. WO 94/09699
PCT Appln. WO 95/06128
PCT Appln. WO 96/39487
Pech et al., *Mol. Cell. Biol.*, 9:396, 1989.
Perez-Stable and Constantini, *Mol. Cell. Biol.*, 10:1116, 1990.
Picard and Schaffner, *Nature*, 307:83, 1984.
Pingoud and Silva, *Nat. Biotechnol.*, 25(7):743-744, 2007.
Pinkert et al., *Genes and Dev.*, 1:268, 1987.
Ponta et al., *Proc. Natl. Acad. Sci. USA*, 82:1020, 1985.
Potrykus et al., *Mol. Gen. Genet.*, 199(2):169-177, 1985.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Redondo et al., *Science*, 247:1225, 1990.
Reisman and Rotter, *Mol. Cell. Biol.*, 9:3571, 1989.
Resendez Jr. et al., *Mol. Cell. Biol.*, 8:4579, 1988.
Rippe et al., *Mol. Cell. Biol.*, 9(5):2224-22277, 1989.
Rippe, et al., *Mol. Cell Biol.*, 10:689-695, 1990.
Rittling et al., *Nucl. Acids Res.*, 17:1619, 1989.
Salmon and Trono, Curr. Protoc. Hum. Genet., 12(Unit 12):10, 2007.
Sambrook and Russell, Molecular Cloning: A Laboratory Manual $3^{rd}$ Ed., Cold Spring Harbor Laboratory Press, 2001.

Schaffner et al., *J. Mol. Biol.*, 201:81, 1988.
Searle et al., *Mol. Cell. Biol.*, 5:1480, 1985.
Sharp and Marciniak, *Cell*, 59:229, 1989.
Shaul and Ben-Levy, *EMBO J.* 6:1913, 1987.
Sherman et al., *Mol. Cell. Biol.*, 9:50, 1989.
Silva et al., *Curr. Gene Ther.*, 11(1): 1-27, 2011.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel. *Biochem. J.*, 248:1, 1987.
Stuart et al., *Nature*, 317:828, 1985.
Sullivan and Peterlin, *Mol. Cell. Biol.*, 7:3315, 1987.
Sun et al., *Biotechniques.* 41:59-63, 2006.
Swartzendruber and Lehman, *J. Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer.* Kucherlapati (Ed.), NY, Plenum Press, 149-188, 1986.
Thiesen et al., *J Virology*, 62:614, 1988.
Treisman, *Cell*, 42:889, 1985.
Tronche et al., *Mol. Biol. Med.*, 7:173, 1990.
Tronche et al., *Mol. Cell. Biol.*, 9:4759, 1989.
Trudel and Constantini. *Genes and Dev.*, 6:954, 1987.
Tur-Kaspa et al., *Mol. Cell Biol.*, 6:716-718, 1986.
Tyndall et al., *Nuc. Acids. Res.*, 9:6231, 1981.
Vasseur et al., *Proc. Natl. Acad. Sci. USA*, 77:1068, 1980.
Wang and Calame, *Cell*, 47:241, 1986.
Weber et al., *Cell*, 36:983, 1984.
Wilson et al., *Science*, 244:1344-1346, 1989.
Winoto and Baltimore, *Cell*, 59:649, 1989.
Wong et al., *Gene*, 10:87-94, 1980.
Wu and Wu, *Biochemistry*, 27: 887-892, 1988.
Wu and Wu, *J. Biol. Chem.*, 262:4429-4432, 1987.
Yamauchi-Takihara, et. al., *Proc. Natl. Acad. Sci. USA*, 86(10):3504-3508, 1989.
Yutzey et al. *Mol. Cell. Biol.*, 9:1397, 1989.
Ziober and Kramer, *J. Bio. Chem.*, 271(37):22915-22, 1996.
Zufferey et al., *Nat. Biotechnol.*, 15(9):871-875, 1997.

The invention claimed is:

1. A recombinant nucleic acid molecule comprising from 5' to 3' and in the order from (a)-(g):
   (a) a flanking sequence;
   (b) a first lower stem sequence which is 12, 13, 14, 15 or 16 nucleotides in length;
   (c) an anti-sense target sequence 22 nucleotides in length;
   (d) a loop sequence;
   (e) a sense sequence wherein the sequence is complementary to the sequence of (c) except that the sequence comprises one or two mismatches relative to the sequence of (c), wherein the one or two mismatches comprise:
      i) a mismatch located at the position 8 to 14 of the sense sequence; or
      ii) a mismatch at the final 3' position (position 22) of the sense sequence;
   (f) a second lower stem sequence wherein the sequence is complementary to the sequence of (b); and
   (g) a second flanking sequence.

2. The nucleic acid molecule of claim 1, wherein the lower stem is 13, 14, 15 or 16 nucleotides in length.

3. The nucleic acid molecule of claim 1, wherein the sense sequence (e) comprises one mismatch relative to sequence (c) located at nucleotide position 11 of the sense sequence (e).

4. The nucleic acid molecule of claim 1, wherein the sense sequence (e) comprises two mismatches relative to sequence (c) located (i) at position 11 of the sense sequence (e) and (ii) at the last 3' nucleotide (position 22) of the sense sequence (e).

5. The nucleic acid molecule of claim 1, comprising a flanking sequence (g), wherein the flanking sequence is not complementary to the flanking sequence (a).

6. The nucleic acid molecule of claim 1, wherein the nucleic acid molecule is RNA.

7. The nucleic acid molecule of claim 1, wherein the nucleic acid molecule is DNA.

8. The nucleic acid molecule of claim 1, wherein the flanking sequence (a) comprises a mir-16 sequence.

9. The nucleic acid molecule of claim 1, wherein the first lower stem sequence (b) comprises a mir-16 sequence.

10. The nucleic acid molecule of claim 9, wherein the first lower stem (b) comprises the mir-16 sequence of SEQ ID NO: 2, SEQ ID NO: 3, SEQ ID NO: 4, SEQ ID NO: 5 or SEQ ID NO: 6.

11. The nucleic acid molecule of claim 1, wherein the mir-16 flanking sequence (a) comprises the sequence of SEQ ID NO: 1.

12. The nucleic acid molecule of claim 1, wherein the loop sequence comprises a mir-30 sequence of SEQ ID NO: 7.

13. The nucleic acid molecule of claim 1, wherein the nucleic acid molecule comprises at least 2 repeats of the sequences (a)-(g).

14. The nucleic acid molecule of claim 1, comprising from 5' to 3' and in the order from (a)-(g):
   (a) a mir-16 flanking sequence;
   (b) a first lower stem sequence comprising a mir-16 sequence;
   (c) an anti-sense target sequence 22 nucleotides in length;
   (d) a mir-30 loop sequence;
   (e) a sense sequence wherein the sequence is complementary to the sequence of (c) except that the sequence comprises one or two mismatches relative to the sequence of (c), wherein the one or two mismatches comprise:
      i) a mismatch located at the position 8 to 14 of the sense sequence; or
      ii) a mismatch at the final 3' position (position 22) of the sense sequence;
   (f) a second lower stem sequence wherein the sequence is complementary to the sequence of (b), wherein the lower stem is at least 11 nucleotides in length; and
   (g) a second flanking sequence.

15. The nucleic acid molecule of claim 14, comprising from 5' to 3' and in the order from (a)-(g):
   (a) a mir-16 flanking sequence comprising the sequence of SEQ ID NO: 1;
   (b) a first lower stem sequence comprising the mir-16 sequence of SEQ ID NO: 2, SEQ ID NO: 3, SEQ ID NO: 4, SEQ ID NO: 5 or SEQ ID NO: 6;
   (c) an anti-sense target sequence 22 nucleotides in length;
   (d) a mir-30 loop sequence comprising the sequence of SEQ ID NO: 7;
   (e) a sense sequence wherein the sequence is complementary to the sequence of (c) except that the sequence comprises one or two mismatches relative to the sequence of (c), wherein the one or two mismatches comprise:
      i) a mismatch located at the position 8 to 14 of the sense sequence; or
      ii) a mismatch at the final 3' position (position 22) of the sense sequence;
   (f) a second lower stem sequence wherein the sequence is complementary to the sequence of (b); and
   (g) a second flanking sequence.

16. The nucleic acid molecule of claim 1, wherein the anti-sense target sequence is complementary to a CCR5 mRNA sequence.

17. An expression vector comprising a nucleic acid of 1 molecule of claim 1 operably linked to a promoter sequence.

18. The expression vector of claim 17, wherein the promoter is an inducible, tissue-specific-or cell lineage-specific promoter.

19. The expression vector of claim 17, further comprising at least one drug resistance marker.

20. A host cell comprising the nucleic acid molecule of claim 1.

21. A method for reducing expression of a gene in a cell comprising expressing a nucleic acid molecule of any one of claim 1 in the cell wherein the anti-sense target sequence (c) is complementary to the sense strand of the gene.

\* \* \* \* \*

UNITED STATES PATENT AND TRADEMARK OFFICE
CERTIFICATE OF CORRECTION

PATENT NO. : 9,556,433 B2
APPLICATION NO. : 14/415201
DATED : January 31, 2017
INVENTOR(S) : Krause et al.

It is certified that error appears in the above-identified patent and that said Letters Patent is hereby corrected as shown below:

In the Claims

In Claim 17, Column 28, Lines 27-28, delete "nucleic acid of 1 molecule of claim 1" and replace with --nucleic acid molecule of claim 1-- therefor.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*